US012671000B2

(12) United States Patent
Perlman et al.

(10) Patent No.: US 12,671,000 B2
(45) Date of Patent: Jun. 30, 2026

(54) SYSTEMS AND METHODS FOR TRANSFORMING AND STORING DATA FROM MULTIPLE STUDIES

(71) Applicant: AIFRED HEALTH, Montreal (CA)

(72) Inventors: Kelly Perlman, Montreal (CA); Caitrin Armstrong, Montreal (CA); Robert Fratila, Montreal (CA); Joseph Mehltretter, Montreal (CA); David Benrimoh, Montreal (CA); Colleen Rollins, Montreal (CA); Jingla-Fri Tunteng, Montreal (CA); Jerome Williams, Montreal (CA); Christina Popescu, Montreal (CA)

(73) Assignee: AIFRED HEALTH, Montreal (CA)

( * ) Notice: Subject to any disclaimer, the term of this patent is extended or adjusted under 35 U.S.C. 154(b) by 0 days.

(21) Appl. No.: 18/963,933

(22) Filed: Nov. 29, 2024

(65) Prior Publication Data

US 2025/0095866 A1 Mar. 20, 2025

Related U.S. Application Data

(63) Continuation of application No. PCT/CA2023/051044, filed on Aug. 4, 2023.

(60) Provisional application No. 63/395,381, filed on Aug. 5, 2022.

(51) Int. Cl.
*G16H 50/70* (2018.01)
*G16H 10/20* (2018.01)

(52) U.S. Cl.
CPC ............. *G16H 50/70* (2018.01); *G16H 10/20* (2018.01)

(58) Field of Classification Search
None
See application file for complete search history.

(56) References Cited

U.S. PATENT DOCUMENTS

| | | | | |
|---|---|---|---|---|
| 9,764,136 | B2 * | 9/2017 | McIntyre | ............... G16H 50/20 |
| 11,328,796 | B1 | 5/2022 | Jain et al. | |
| 11,605,463 | B2 * | 3/2023 | Armstrong | ............. G16H 20/10 |

(Continued)

FOREIGN PATENT DOCUMENTS

| | | | | |
|---|---|---|---|---|
| CN | 114822874 A | * | 7/2022 | ............. G06N 3/045 |

OTHER PUBLICATIONS

Tarang Shah, About train, validation and test sets in machine learning, Towards Data Science, Dec. 6, 2017, https://towardsdatascience.com/train-validation-and-test-sets-72cb40cba9e7.

(Continued)

*Primary Examiner* — Robert A Sorey
(74) *Attorney, Agent, or Firm* — BCF LLP

(57) ABSTRACT

There is disclosed a method and system for combining datasets. Study results may be retrieved. Each study result may include datapoints. Each datapoint may include attributes. Study questions may be extracted from the study results. The questions may be converted into a standardized format. Categories may be assigned to the questions. The questions may be grouped together into groups. A response scale may be determined for each of the groups. The responses may be rescaled using the corresponding response scale. A final dataset may be generated by combining the study results. Features may be selected using the final dataset. A machine learning algorithm may be trained using the features of the final dataset.

20 Claims, 5 Drawing Sheets

(56) References Cited

U.S. PATENT DOCUMENTS

| | | | | |
|---|---|---|---|---|
| 2014/0052474 A1* | 2/2014 | Madan | .................. | G16H 50/50 |
| | | | | 705/3 |
| 2018/0232486 A1* | 8/2018 | Carpenter | .............. | A61B 5/316 |
| 2019/0267112 A1* | 8/2019 | Taliaz | ................... | G16H 10/60 |
| 2019/0341152 A1* | 11/2019 | Mellem | ................. | G16H 50/70 |
| 2021/0201144 A1 | 7/2021 | Jonnalagadda et al. | | |
| 2021/0236044 A1* | 8/2021 | Arroyo-Gallego | .... | A61B 5/225 |

OTHER PUBLICATIONS

International Search Report and Written Opinion issued in corresponding International application No. PCT/CA2023/051044 on Oct. 19, 2023.

* cited by examiner

SYSTEMS AND METHODS FOR TRANSFORMING AND STORING DATA FROM MULTIPLE STUDIES

CROSS-REFERENCE TO RELATED APPLICATIONS

This application is a continuation of International Application No. PCT/CA2023/051044, filed on Aug. 4, 2023, which claims the benefit of U.S. Provisional Patent Application No. 63/395,381, filed Aug. 5, 2022, each of which is incorporated by reference herein in its entirety.

BACKGROUND

Medical studies for a same medical condition may collect different data from patients in the studies. The studies may have the patients complete different clinical questionnaires. The data from the different medical studies may be used to compare different treatment options. It may be desirable to train a machine learning algorithm to predict outcomes for the different treatment options used in the studies. Because the studies use different methodologies for collecting data about the patients, it might not be possible to combine data from multiple studies to train the machine learning algorithm.

SUMMARY

Multiple studies may relate to a same or similar medical condition. Different studies may study different treatments and/or treatment protocols for the medical condition. Each study collects various information about the patients participating in the study. Similar and/or overlapping data may be collected by each study, but this data may be collected in different formats.

In order to gather information about patients participating in a study, the patients may be given clinical questionnaires. The different studies may use different questionnaires and/or different forms of the questionnaires. For example patients enrolled in a first study may be given a short-form version of a questionnaire and patients enrolled in a second study may be given a long-form version of the questionnaire. Even within a single study, different questionnaires and/or different formats of a questionnaire may be used.

A machine learning algorithm (MLA) may be trained using data from the different studies. In order to prepare the data to be used to train the MLA, the data from the different studies may be converted into a common format. Questions that are identical or nearly identical may be merged into a standardized format. Each question may be categorized and similar questions may be combined.

Data from multiple studies may be retrieved and then used to generate a dataset that can be used for training an MLA. A set of data points may be extracted from each study, where each data point includes data corresponding to a single patient. Each data point may include various attributes of the patient extracted from the study data. The attributes may include data collected using clinical questionnaires. The individual questions that were in the questionnaire may be extracted from the study.

Standardized questions may be created based on the questions from the questionnaires used in the studies. Each question asked in the study may be converted into one of the standardized questions. A taxonomy with various categories may be defined. Each of the standardized questions may be assigned a category or categories from the taxonomy. The standardized questions may also be assigned flags.

Questions that are compatible may be identified because they have same or similar categories assigned to them. The compatible questions may be grouped together and combined. The responses for the grouped questions may be rescaled into a common scale. The scale may be a categorical or binary scale. Whether the scale for a question is categorical or binary may be determined based on the format of the questions that are being combined. After rescaling the questions in the group into a common scale, the grouped questions may be combined.

The study data may have some missing data. For example a data point in a study may be missing a value for an attribute. This missing data may be imputed. If the amount of data missing from a study is over a pre-defined threshold, individual attributes that have a high amount of missing data may be removed from the study or the entire study may be removed.

After combining and rescaling the questions, a final dataset may be generated. The final dataset may be split into a training set, validation set, and/or testing set. The training set may be used to select features for the MLA. The features may be one or more categories from the taxonomy, attributes from the study data, and/or responses to questionnaires.

The MLA may be trained using the selected features from the training set. After being trained, the MLA may be adjusted using the validation set. Then, the MLA may be tested using the testing set.

According to a first broad aspect of the present technology, there is provided a method comprising: retrieving a plurality of study results, wherein each study result comprises a plurality of datapoints, and wherein each datapoint comprises a plurality of attributes; extracting a plurality of questions from the plurality of study results; converting the plurality of questions into questions in a standardized format; assigning one or more categories to each of the plurality of questions; determining, based on the one or more categories assigned to each question, a plurality of groups of questions; determining a response scale to use for each group of the plurality of groups; rescaling responses to the groups of questions based on the respective response scale of the group; combining questions for each group of the plurality of groups; imputing missing attribute values in the plurality of study results; generating a final dataset by combining the plurality of study results; splitting the final dataset into a training set, validation set, and testing set; selecting, based on the training set, a plurality of features in the training set; and training a machine learning algorithm (MLA) using the plurality of features of the training set.

In some implementations of the method, the plurality of questions comprise questions from clinical questionnaires given to patients enrolled in clinical trails.

In some implementations of the method, each datapoint corresponds to a patient enrolled in a clinical trial, and wherein the plurality of attributes comprise an indication of a treatment given to the patient.

In some implementations of the method, the plurality of attributes comprise an indication of responses to a clinical questionnaire given to the patient.

In some implementations of the method, the plurality of attributes comprise an indication of whether the treatment is effective for the patient.

In some implementations of the method, the plurality of attributes comprise an indication of side effects experienced by the patient.

In some implementations of the method, the plurality of attributes comprise physiological data of the patient.

In some implementations of the method, the plurality of attributes comprise historical data of the patient.

In some implementations of the method, the plurality of attributes comprise sociodemographic data of the patient.

In some implementations of the method, the plurality of attributes comprise psychological data of the patient.

In some implementations of the method, rescaling responses to the groups of questions comprises using equi-percentile scaling to rescale the responses.

According to another broad aspect of the present technology, there is provided a method comprising: retrieving a plurality of study results, wherein each study result comprises a plurality of datapoints, and wherein each datapoint comprises a plurality of attributes; extracting a plurality of questions from the plurality of study results; converting the plurality of questions into questions in a standardized format; assigning one or more categories to each of the plurality of questions; determining a group of questions, of the plurality of questions, that have a same set of assigned categories; combining the group of questions; generating a final dataset by combining the plurality of study results; selecting a plurality of features in the final dataset; and training a machine learning algorithm (MLA) using the plurality of features.

In some implementations of the method, combining the group of questions comprises: determining a response scale for the group of questions; and rescaling responses corresponding to the group of questions based on the response scale.

According to a further broad aspect of the present technology, there is provided a method for predicting treatment efficacy for a patient, the method comprising: receiving questionnaire responses from the patient; inputting the questionnaire responses into an MLA trained according to any of the methods described herein; outputting, by the MLA, a predicted efficacy of each of the plurality of treatments; generating, based on the predicted efficacy of each of the plurality of treatments, an interface; and outputting for display the interface.

According to another broad aspect of the present technology, there is provided a trained MLA which is trained in accordance with any of the methods described and claimed herein.

According to another broad aspect of the present technology, there is provided a method for a patient (such as for predicting treatment efficacy), the method comprising: training a machine learning algorithm (MLA) by: retrieving a plurality of study results corresponding to a plurality of treatments, wherein each study result comprises a plurality of datapoints, and wherein each datapoint comprises a plurality of attributes, extracting a plurality of questions from the plurality of study results, converting the plurality of questions into questions in a standardized format, assigning one or more categories to each of the plurality of questions, determining a group of questions, of the plurality of questions, that have a same set of assigned categories, combining the group of questions, generating a final dataset by combining the plurality of study results, and training the MLA using the final dataset; receiving questionnaire responses from the patient; inputting the questionnaire responses into the MLA; outputting, by the MLA, a predicted efficacy of each of the plurality of treatments; generating, based on the predicted efficacy of each of the plurality of treatments, an interface; and outputting for display the interface.

Various implementations of the present technology provide a computer-based system, such as, for example, but without being limitative, an electronic device comprising at least one processor and a memory storing program instructions for executing one or more methods described herein, the program instructions being executable by the at least one processor of the electronic device.

It should be expressly understood that not all technical effects mentioned herein need be enjoyed in each and every embodiment of the present technology.

As used herein, the wording "and/or" is intended to represent an inclusive-or; for example, "X and/or Y" is intended to mean X or Y or both. As a further example, "X, Y, and/or Z" is intended to mean X or Y or Z or any combination thereof.

In the context of the present specification, unless expressly provided otherwise, a computer system or computing environment may refer, but is not limited to, an "electronic device," a "computing device," an "operation system," a "system," a "computer-based system," a "computer system," a "network system," a "network device," a "controller unit," a "monitoring device," a "control device," a "server," and/or any combination thereof appropriate to the relevant task at hand.

In the context of the present specification, unless expressly provided otherwise, any of the methods and/or systems described herein may be implemented in a cloud-based environment, such as, but not limited to, a Microsoft Azure environment, an Amazon EC2 environment, and/or a Google Cloud environment.

In the context of the present specification, unless expressly provided otherwise, the expression "computer-readable medium" and "memory" are intended to include media of any nature and kind whatsoever, non-limiting examples of which include RAM, ROM, disks (e.g., CD-ROMs, DVDs, floppy disks, hard disk drives, etc.), USB keys, flash memory cards, solid state-drives, and tape drives. Still in the context of the present specification, "a" computer-readable medium and "the" computer-readable medium should not be construed as being the same computer-readable medium. To the contrary, and whenever appropriate, "a" computer-readable medium and "the" computer-readable medium may also be construed as a first computer-readable medium and a second computer-readable medium.

In the context of the present specification, unless expressly provided otherwise, the words "first," "second," "third," etc. have been used as adjectives only for the purpose of allowing for distinction between the nouns that they modify from one another, and not for the purpose of describing any particular relationship between those nouns.

Additional and/or alternative features, aspects and advantages of implementations of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
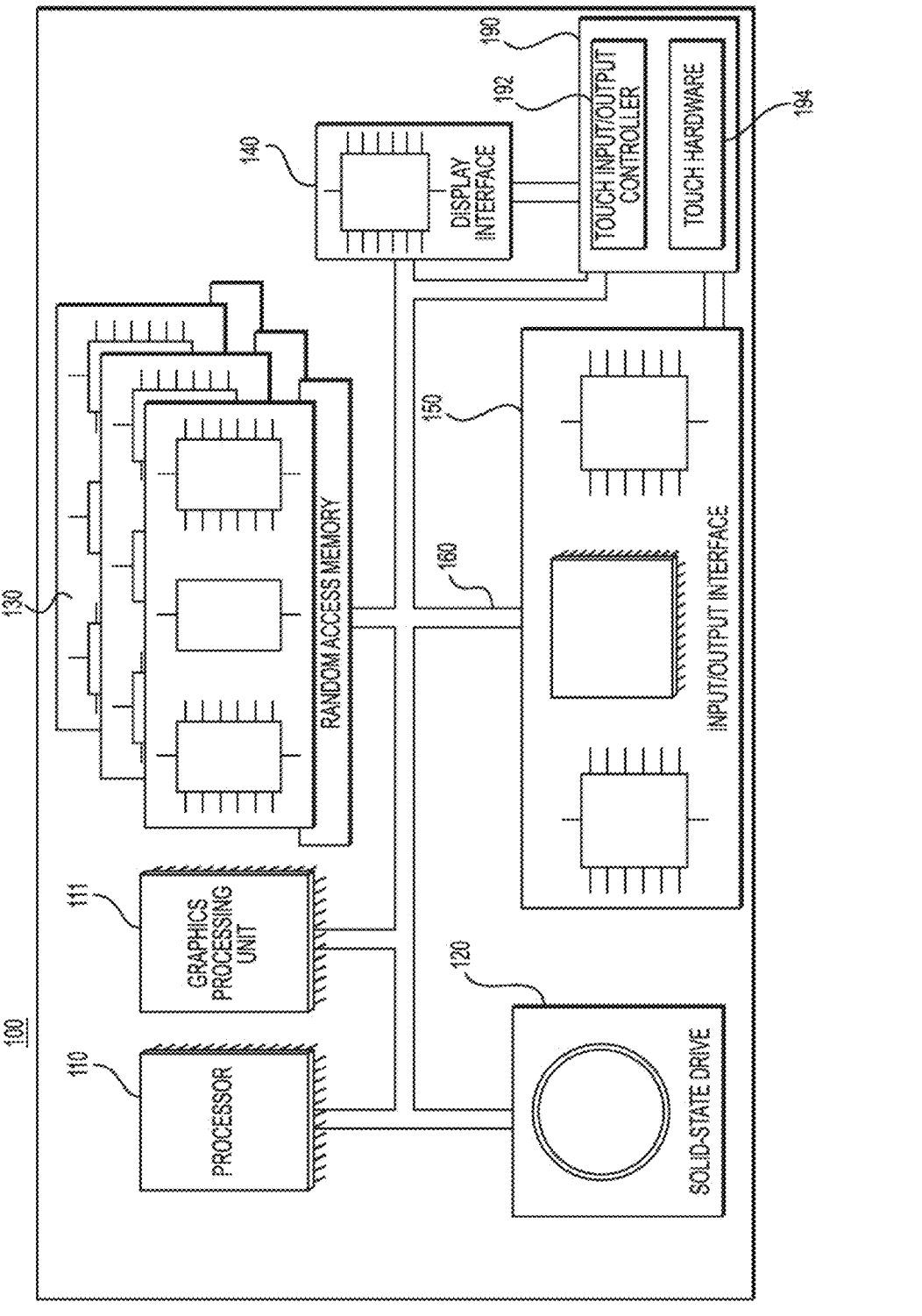
FIG. 1 is a block diagram of an example computing environment in accordance with various embodiments of the present technology.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor," may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Moreover, it should be understood that one or more modules may include for example, but without being limitative, computer program logic, computer program instructions, software, stack, firmware, hardware circuitry, or a combination thereof.

Computing Environment

FIG. 1 illustrates a computing environment 100, which may be used to implement and/or execute any of the methods described herein. In some embodiments, the computing environment 100 may be implemented by any of a conventional personal computer, a computer dedicated to managing network resources, a network device and/or an electronic device (such as, but not limited to, a mobile device, a tablet device, a server, a controller unit, a control device, etc.), and/or any combination thereof appropriate to the relevant task at hand. In some embodiments, the computing environment 100 comprises various hardware components including one or more single or multi-core processors collectively represented by processor 110, a solid-state drive 120, a random access memory 130, and an input/output interface 150. The computing environment 100 may be a computer specifically designed to operate a machine learning algorithm (MLA). The computing environment 100 may be a generic computer system.

In some embodiments, the computing environment 100 may also be a subsystem of one of the above-listed systems. In some other embodiments, the computing environment 100 may be an "off-the-shelf" generic computer system. In some embodiments, the computing environment 100 may also be distributed amongst multiple systems. The computing environment 100 may also be specifically dedicated to the implementation of the present technology. As a person in the art of the present technology may appreciate, multiple variations as to how the computing environment 100 is implemented may be envisioned without departing from the scope of the present technology.

Those skilled in the art will appreciate that processor 110 is generally representative of a processing capability. In some embodiments, in place of or in addition to one or more conventional Central Processing Units (CPUs), one or more specialized processing cores may be provided. For example, one or more Graphic Processing Units (GPUs), Tensor Processing Units (TPUs), and/or other so-called accelerated processors (or processing accelerators) may be provided in addition to or in place of one or more CPUs.

System memory will typically include random access memory 130, but is more generally intended to encompass any type of non-transitory system memory such as static random access memory (SRAM), dynamic random access memory (DRAM), synchronous DRAM (SDRAM), read-only memory (ROM), or a combination thereof. Solid-state drive 120 is shown as an example of a mass storage device, but more generally such mass storage may comprise any type of non-transitory storage device configured to store data, programs, and other information, and to make the data, programs, and other information accessible via a system bus

160. For example, mass storage may comprise one or more of a solid state drive, hard disk drive, a magnetic disk drive, and/or an optical disk drive.

Communication between the various components of the computing environment 100 may be enabled by a system bus 160 comprising one or more internal and/or external buses (e.g., a PCI bus, universal serial bus, IEEE 1394 "Firewire" bus, SCSI bus, Serial-ATA bus, ARINC bus, etc.), to which the various hardware components are electronically coupled.

The input/output interface 150 may allow enabling networking capabilities such as wired or wireless access. As an example, the input/output interface 150 may comprise a networking interface such as, but not limited to, a network port, a network socket, a network interface controller and the like. Multiple examples of how the networking interface may be implemented will become apparent to the person skilled in the art of the present technology. For example the networking interface may implement specific physical layer and data link layer standards such as Ethernet, Fibre Channel, Wi-Fi, Token Ring or Serial communication protocols. The specific physical layer and the data link layer may provide a base for a full network protocol stack, allowing communication among small groups of computers on the same local area network (LAN) and large-scale network communications through routable protocols, such as Internet Protocol (IP).

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the computing device 100 in addition to or instead of the touchscreen 190.

According to some implementations of the present technology, the solid-state drive 120 stores program instructions suitable for being loaded into the random access memory 130 and executed by the processor 110 for executing acts of one or more methods described herein. For example, at least some of the program instructions may be part of a library or an application.

Combining Study Results

Figure 2:
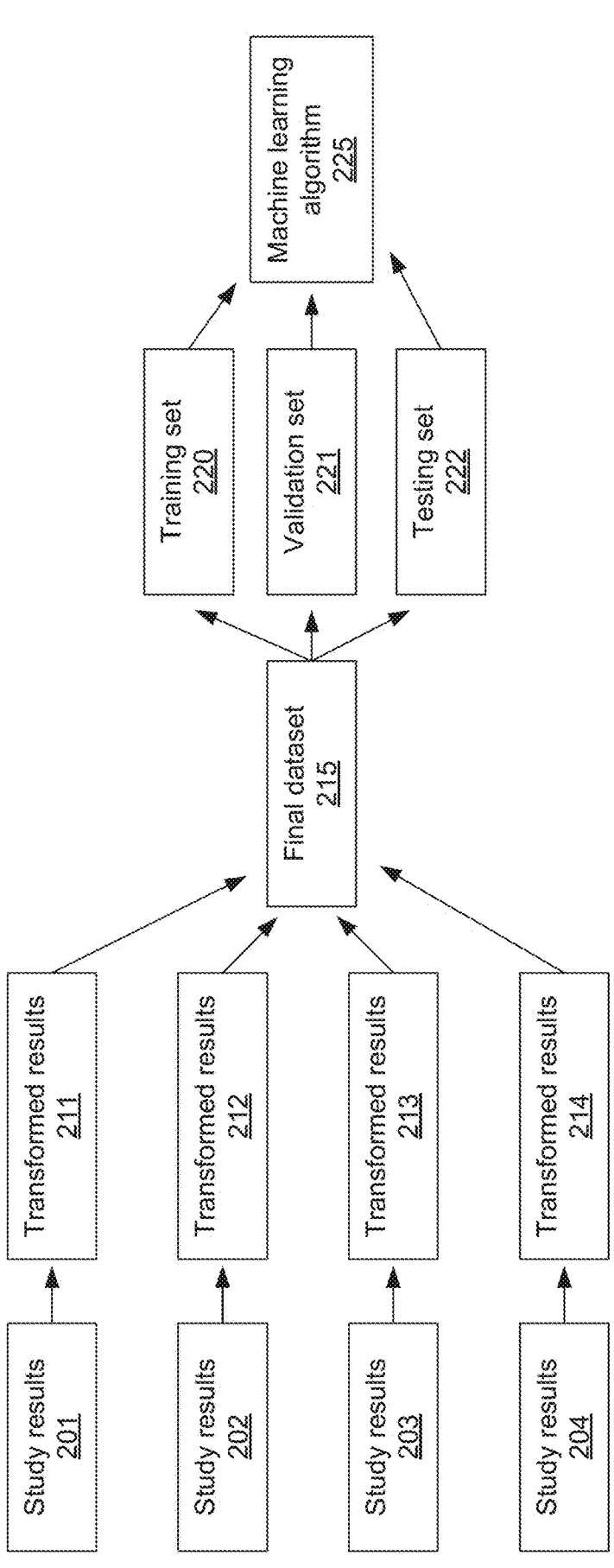
FIG. 2 is a diagram of a process for combining study results to train a machine learning algorithm (MLA) in accordance with various embodiments of the present technology.

FIG. 2 is a diagram of a process for combining study results to train a machine learning algorithm (MLA) in accordance with various embodiments of the present technology. Study results 201-04 may be retrieved. Each of the studies may have tested the effects of a different treatment and/or treatment protocol on a same medical condition. For example, the study results 201 may be the results of a study of a compound being used to treat depression, and the study results 202 may be the results of a study of a different compound being used to treat depression.

Although described as study results 201-04, it should be understood that the methods described herein may be used to combine any type of datasets that have common data that may be in different formats. The datasets to be combined may be the results of a clinical trial and/or any other type of dataset. The data to be combined may include any type of patient data, such as electronic medical records (EMR). For example attributes of a patient, treatment information about the patient, and outcome data corresponding to the treatments may be extracted from the patient's EMR and then combined with data extracted from other patients' EMRs.

Each set of study results 201-04 may include a set of datapoints regarding the individual patients involved in each study. Each datapoint corresponds to an individual patient that was enrolled in the study. The datapoints may include various attributes. The attributes of a datapoint corresponding to a patient may include the patient's responses to clinical questionnaires, information about the patient, information about the treatment applied to the patient, outcome data indicating the patient's response to the treatment, the patient's medical history, the patient's family history, physiological information about the patient, and/or any other data collected regarding the patient.

The outcome data of a datapoint may include whether the treatment led to remission, an amount of time to remission, whether the treatment caused harm and/or had harmful side effects, whether the treatment resolved certain symptoms, whether the treatment led to a return to a base line physiological measurement, and/or any other measure of the treatment's efficacy.

The different studies that resulted in study results 201-04 may have used the same and/or different questionnaires. Even if different questionnaires were used, or different formats of questionnaires were used, the different questionnaires may have similar questions. For example, a questionnaire used in a first study and a questionnaire in a second study may ask different questions about a same topic.

The clinical questionnaires may include questions relating to the patient's mental health, medical history, family medical history, current medications, sociodemographic information, and/or any other type of questions. The patient may be periodically asked to update the clinical questionnaire and/or complete a new clinical questionnaire, so that the information collected regarding the patient is up-to-date. Accordingly, an individual datapoint in the study results 201-04 may include multiple responses, given at different times, to a same questionnaire. A patient may be asked to update the clinical questionnaire after a pre-determined amount of time has passed. The clinical questionnaire may be completed by the patient, a caregiver of the patient, and/or a doctor.

Standardized versions of the question in the study results 201-04 may be generated. Similar, but not identical, questions may be asked in different studies and/or different questionnaires. Questions that are similar may be grouped together and replaced with a standardized version of that question in the transformed results 211-14.

Figure 3:
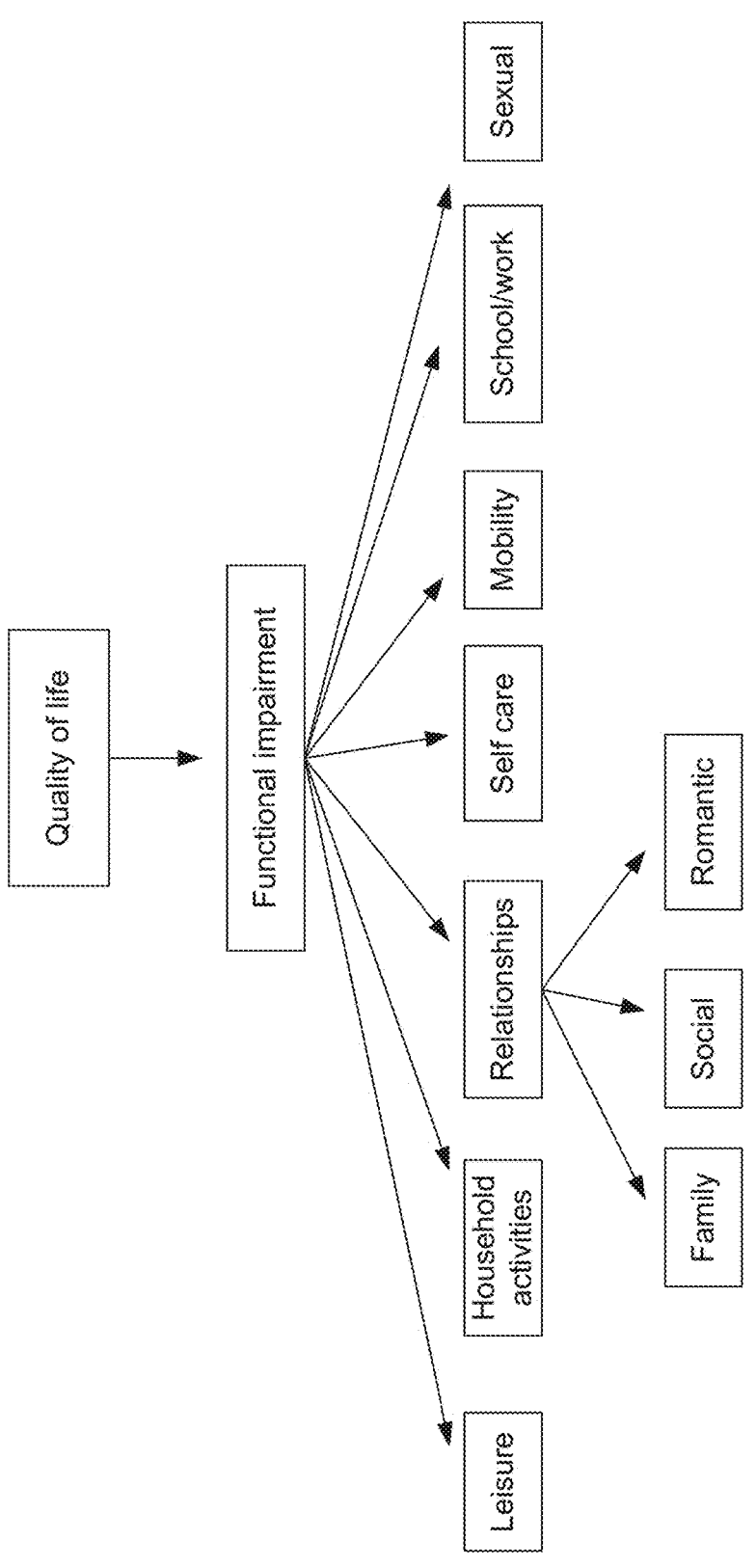
FIG. 3 illustrates a diagram of a taxonomy in accordance with various embodiments of the present technology.

A taxonomy of categories may be generated and/or predefined. The categories may be categories of questions in the questionnaires. The taxonomy may be organized in a tree structure, where each category can have a parent node and/or child nodes. FIG. 3 shows an example of a taxonomy. In the taxonomy shown in FIG. 3, the "functional impairment" category is a branch of the "quality of life" root category. The "functional impairment" category has further leaves and another sub-branch, relationships, which itself has the leaves "family", "social", and "romantic".

The questions in the study results 201-04 may each be assigned one or more of the categories in the taxonomy. The questions may be assigned categories based on keywords in the questions. The categories may be assigned to questions using an MLA, based on a manual review and/or based on any other suitable method. An MLA may be trained to assign categories to a question based on the text of the question. A question may be input to the MLA and the MLA may output one or more categories that are predicted to correspond to the question. A human operator may then confirm that the predicted categories correspond to the question and/or edit the categories that were assigned to the question. Other methods may be used for suggesting categories to apply to a question, such as by extracting individual words from the question.

After standardizing the questions and categorizing them, questions that are compatible with each other may be grouped together and then combined. The compatible questions may be semantically analogous to each other. Groups of questions may be formed that have same and/or similar categories assigned to them. For each group of questions, a common response format may be selected. The responses for the questions in the group may be rescaled into the selected format. After rescaling the responses, the grouped questions may be combined.

The study results 201-04 may be transformed into transformed results 211-14. In the transformed results 211-14, each of the questions may be in a standardized format. Questions that were analogous may be transformed into the combined version of the question.

The transformed results 211-14 of each study may then be combined into the final dataset 215. Because the study results 201-04 have been transformed into a common format in the transformed results 211-14, the data may be able to be combined in the final dataset 215. The final dataset 215 may include datapoints from each of the study results 201-04. Each datapoint in the final dataset 215 may be associated with an individual patient. Each datapoint may include attributes that indicate the standardized and transformed questions, the treatment that the patient received, and an indication of the efficacy of the treatment on the patient.

The final dataset 215 may be split into a training set 220, validation set 221, and testing set 222. The training set 220, validation set 221, and testing set 222 may each include a subset of the datapoints in the final dataset 215. Each datapoint in the final dataset 215 may be randomly assigned to the training set 220, validation set 221, or testing set 222. The training set 220, validation set 221, and testing set 222 may have pre-determined sizes. For example, the training set 220 may be configured to be larger than the validation set 221.

After generating the training set 220, an MLA 225 may be trained using the training set 220. Each datapoint in the training set 220 may be input to the MLA 225. The MLA 225 may predict the likelihood of remission for a patient corresponding to the datapoint if the patient is given various treatments. For each potential treatment, the MLA 225 may output a predicted likelihood of remission.

The MLA 225 may comprise one or more neural networks and/or any other type of machine-learning, deep learning, and/or artificial intelligence (AI) model. The MLA 225 may include an encoder whose input, x, lacks the treatment assigned to the patient and is responsible for encoding features corresponding to the patient into some latent space, e (x). A decoder may decode back the encoded features to the original input, d (e (x)). The decoded features might not be identical to the original features that were encoded. Any suitable type of encoder and/or decoder may be used, such as a symmetrical auto-encoder.

A loss function may compare the predicted efficacy of the treatment to the actual outcome recorded during the study, which is stored in the training set 220. The actual outcome may be referred to as the "label" for a datapoint, and the MLA 225 may be trained to predict the label. The MLA 225 may then adjust itself based on the amount of loss output by the loss function. The MLA 225 may be adjusted to reduce the amount of loss between the prediction and the label. This training process may be repeated for every datapoint in the training set 220.

After the MLA 225 has been trained using the training set 220, the validation set 221 may be used to adjust the MLA 225. Each datapoint in the validation set 221 may be input to the MLA 225. The MLA 225 may then output a predicted outcome, which may be compared to the corresponding label using the loss function. Parameters of the MLA 225 may be adjusted based on the outcome of the loss function.

After adjusting the MLA 225 using the validation set 221, the testing set 222 may be input to the MLA 225 to determine how accurate the predictions of the MLA 225 are. Various methods may be used to determine whether the MLA 225 is sufficiently accurate for further use. The predictions output by the MLA 225 may be compared to the outcomes in the testing set 222. The average amount of loss of the MLA 225 for the testing set 222 may be determined. If the average amount of loss is less than a pre-determined threshold amount of loss, the MLA 225 may be determined to be ready for use.

In order to use the MLA 225 after the MLA 225 has been trained, a clinical questionnaire may be administered to a patient. Answers to the questions may be encoded into a vector of numbers using an encoder function e (x). The vector may then be input to the MLA 225.

Prototypes

Various prototypes may be defined corresponding to clusters of patients. Each prototype may correspond to a group of patients that have similar characteristics, present similar symptoms and/or respond similarly to one or more treatments. The prototypes may be defined so that each prototype responds differently to the available treatments. The prototypes may assist the clinician and/or patient in understanding the results that are output by the MLA 225. In other words, the prototypes may be used to enhance the interpretability of the results for the clinician and/or patient. Each prototype may be used to generate an exemplary patient corresponding to the prototype in order to compare a real patient to this prototype.

The training of the MLA 225 may involve a layer of a neural network forming the MLA 225 that extracts these prototypes. Each prototype may indicate the importance of features in predicting remission for patients and/or the differential effect of different treatments on a given prototype. Each prototype may be associated with a patient cluster, meaning the group of patients that are relatively similar to the learned prototypes. The prototype extraction may improve the accuracy of the MLA 225 and/or to improve the interpretability of the MLA 225. The prototype extraction may assist clinicians in understanding outputs of the MLA 225 by demonstrating how different feature clusters, representing different patient prototypes, might respond to different treatments.

The number of prototypes to be defined may be determined empirically (with human/non-human initialization and experiment progression) and/or dynamically (through algorithmic determinism to optimize a downstream objective). The number of prototypes may be selected based on various considerations, such as increasing interpretability and/or accuracy of the prototypes. For example, the number of prototypes may be set to three, which may provide a balance between providing enough nuance between the prototypes while also providing a sufficiently accurate MLA 225.

In some instances, the prototypes may be defined in the original feature space without use of the auto-encoder but then encoded, by the auto-encoder, into the latent space for compatibility in the comparison with already encoded features. The prototypes may be defined manually by an operator and/or automatically using various functions, such as clustering algorithms. For example an operator may input various parameters for a prototype.

Given the symmetrical nature of the neural network, the encoder and decoder may both include the same number of fully-connected layers. The encoding layer's, e (x), output may be fed into a prototype layer, p, which may be configured with k-nodes to represent each prototype separately. The variable k may represent the number of patient archetypes that the prototypes may, separately, learn to represent. Each node may be the size of the incoming data samples. The prototypes may be defined in the latent (encoded) space.

In order for a patient's data to be compared to the set of prototypes, they both can be mapped to the encoded space. The prototypes may have learned parameters which can be configured to shift around the encoded feature space in order to achieve optimal down-stream predictive performance of the MLA. The prototypes may be assigned "frozen" weights which may ensure that the prototypes remain static throughout the duration of the MLA training.

In order to render the prototypes interpretable by an operator, such as a clinician, the prototypes may be decoded by the decoder, d (p). The decoder may extract the original feature values corresponding to a prototype. A content expert, such as a clinician, may review the original feature values for prototypes to better understand the prototypes and their relationship with predicted treatment effectiveness probabilities.

When a patient's data is input to the MLA 225, the auto-encoder may be used in order to calculate the distance between the patient and each of the prototypes in latent space. These distances may then be passed down for downstream predictive objectives.

Prototype Configuration

Various hyperparameters may be configured when defining the prototypes, including (1) the number of prototypes that the MLA 225 will support and (2) the tunable parameters for each prototype.

Any number of prototypes may be defined. For the purpose of improving interpretability, it may be preferable to have a relatively smaller number of prototypes, such as two, three, or four prototypes because having too many prototypes may make it difficult for a clinician to understand and/or explain why a patient might benefit from one treatment over another. From a performance perspective, the number of prototypes may also be configured to optimize a downstream objective such as predicting a remission rate for a treatment. An operator may select the number of prototypes to define in order to balance interpretability and the overall performance of the MLA 225.

The parameters for a prototype can be defined in various ways, such as based on input from an operator and/or automatically using functions. An operator may define parameters for a prototype. A prototype may then be generated based on the parameters defined by the operator. The parameters for a prototype may be generated using functions, such as clustering algorithms.

Previously identified stereotypical patient clusters may be used as the basis for prototypes. An operator may define parameters corresponding to the previously identified clusters, and the previously identified clusters may be translated into prototypes by passing those parameter values through the encoder e (x) in order to initialize the prototypes.

Algorithmic initialization may be used to generate the prototypes. Prototypes may be initialized using the Xavier-Glorot uniform/normal, He (i.e. Kaiming) uniform/normal, or a normal or uniform, or other pre-existing or custom distribution that allows the sampling of a set of parameters from a continuous or discrete set of values.

Prototype Output

The output of the prototype layer may represent the distance between a patient's encoded data, e(x), and each of the prototypes, p. In other words, the output may indicate a distance between the patient and each of the prototypes. This distance may be defined by the Frobenius norm between the encoded sample and each of the prototypes, separately. Any other suitable distance measure may be used, such as variance-based distance (under the assumption that each prototype represents a statistically different distribution of samples), Mahalanobis distance, or modelling each of the prototype clusters to a normal distribution to identify which patient samples are most likely to belong within some standard deviation of the cluster centers. For example, if a sample is more likely to be within one standard deviation of a first cluster than the third standard deviation of a second cluster, the distances may reflect that degree of overlap.

The patient-to-prototype latent distances may be fed into a fully connected neural layer that gets concatenated with the assigned treatment that was omitted before passing in patient information to the encoder. The treatments may be encoded in a one-hot fashion before being concatenated to the rest of the distance vector. This concatenation may feed into the final classification layers whose objective is to extract the likelihood of remission for each of the assigned treatments to test the hypothetical cases for each of the patients. These predicted remission rates for each treatment for each of the patients may then be aggregated and used to calculate the differential benefit.

Method for Generating a Combined Dataset

Figure 4:
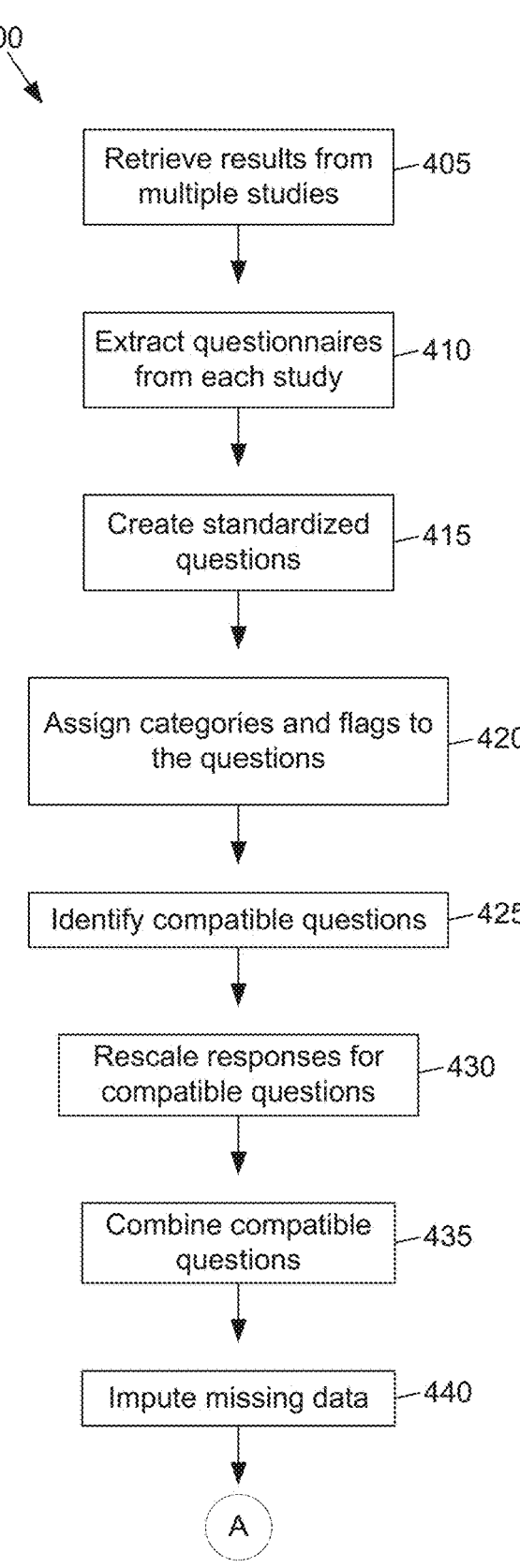
FIGS. 4 and 5 illustrate a flow diagram of a method for generating a combined dataset in accordance with various embodiments of the present technology.
Figure 5:
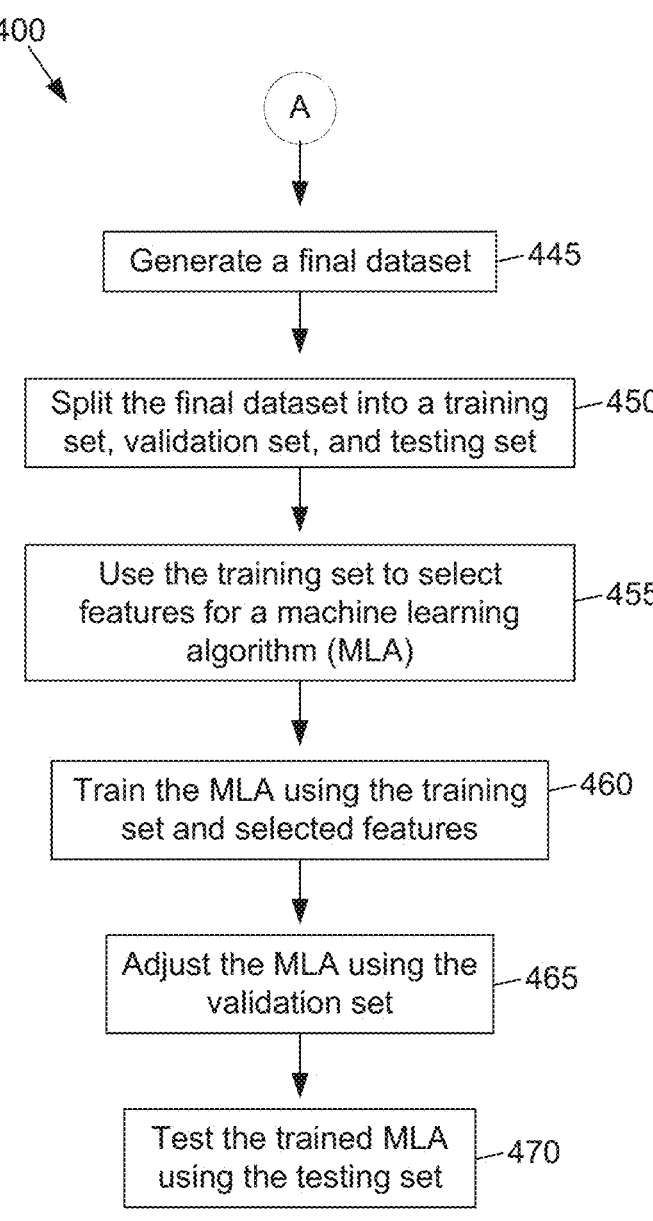

FIGS. 4 and 5 illustrate a flow diagram of a method 400 for generating a combined dataset in accordance with various embodiments of the present technology. In one or more aspects, the method 400 or one or more steps thereof may be performed by a computing system, such as the computing environment 100. The method 400 or one or more steps thereof may be embodied in computer-executable instructions that are stored in a computer-readable medium, such as a non-transitory mass storage device, loaded into memory and executed by a CPU. Some steps or portions of steps in the flow diagram may be omitted or changed in order.

At step 405 data may be retrieved from multiple studies, such as the study results 201-04. As described above, the studies may be clinical studies that tested various treatments for a medical condition. The retrieved data may be de-identified patient-level data from clinical trials of treatment for a condition, such as depression. The data may include the relevant study protocols corresponding to the study.

Patients enrolled in the studies may have completed clinical questionnaires. The studies may have used different questionnaires and/or different formats of the questionnaires. Different patients may have been given different questionnaires and/or different formats of the questionnaires. The data retrieved at step 405 may include the answers to the questionnaires given by the patients. The data retrieved at step 405 may include the outcome of the study for each patient. The outcome of the study for each patient may include an indication as to whether the treatment was effective for the patient, and/or a measure of how effective the treatment was for the patient. The data retrieved at step 405 may include indirect measures of treatment effectiveness such as quality of life evaluations, functional impairment scaled, and/or any other indirect measures.

At step 410 the questionnaires may be extracted from each of the study results 201-04. In some instances, a single questionnaire may be extracted from one of the study results 201-04. In other instances, multiple questionnaires may be extracted from one of the study results 201-04. The extracted questionnaires may include each individual question that was asked to the participants of the study. Each question may be associated with information about the available responses. The information about the available responses may indicate whether the participants were able to provide a binary or categorical response to a question. A binary response is a response where the patient was able to select "yes" or "no," "true" or "false," or any other binary response. A categorical response is a response in which the patient is able to select from multiple responses and/or select from a response on a scale, such as a Likert scale. An example of a question with a categorical response is a question that asks the patient to provide a rating of one to five. The information about the available response for a categorical question may include a scale corresponding to the response, information about the options that were available to the patient to respond, and/or information indicating the meaning of the highest and lowest values on the scale.

At step 415 standardized questions may be created. Each question extracted at step 410 may be converted into a standardized format. A standard question text may be created for each question. Different questionnaires may include a same question in a slightly different format and/or the questions may be in a different order. A single standard version of the question may be selected, and all of the other iterations of that question may be matched to the standard version.

Different studies may use slightly different versions of a same questionnaire. The different versions of the questionnaire may include a similar set of questions, but the text of the questions may be slightly different and/or the order of the questions may be different. A single version of the questionnaire may be selected as the standard version of the questionnaire. Response to all other iterations of the questionnaire that were used may be modified to match the standard version of the questionnaire.

At step 420 each of the standardized questions may be assigned categories and/or flags. The categories may be categories in a taxonomy, such as the taxonomy of categories illustrated in FIG. 3. It should be noted that the taxonomy illustrated in FIG. 3 is exemplary, and that the actual taxonomy used may include any number of categories and/or levels. The taxonomy may include categories relating to sociodemographic, physiological, cognitive, and quality of life features, and/or any other type of category.

Each question may be assigned a root category. Then, child categories of the root category that correspond to the question may be assigned to the question.

One or more flags may be selected for each question. The flags may represent various characteristics of the question, such as whether the question was answered by a patient or a clinician, whether the question refers to a current time or a past time, and/or any other aspects of the question. The available flags may be pre-defined flags.

The categories may be applied manually and/or automatically. A semantic system may be used to apply and/or suggest categories corresponding to a question. An administrator may select from the suggested categories and/or apply other categories. If a selected category has parent categories, those parent categories may be assigned automatically to the question. For example, using the taxonomy illustrated in FIG. 3, if the "Family" category is assigned to a question, then the parent categories "Relationships," "Functional impairment," and "Quality of life" may also be assigned to the question.

At step 425 compatible questions may be identified and grouped together. Questions that have same or similar categories may be grouped together. An administrator may review the questions that have been grouped together to determine whether they are compatible. The administrator may modify the grouped questions, such as by adding or removing questions from the group.

Questions that have a same type of response, categorical or binary, may be grouped together. Questions that do not have the same type of response might not be grouped together. For example a question with a categorical response might not be determined to be compatible with a question that has a binary response, even if they would have been considered compatible if they had the same type of response.

At step 430 the responses for compatible questions that have been grouped together may be rescaled. A single scale may be determined and applied to all of the questions in a group. For example if two questions in a group have responses that range from one to ten, and another question in the group has responses ranging from one to five, the responses ranging from one to five may be rescaled to range from one to ten. Any suitable method of rescaling may be used, such as equipercentile equating. Equipercentile equating is an equating method which uses the underlying value percentiles between two variables to convert one scale to be on the same scale as the other variable.

If a group has both binary and categorical questions, the questions may be all rescaled into either the binary format or the categorical format. For example, for a group with binary and categorical questions, the categorical responses may be transformed into binary responses.

At step 435 the compatible questions may be combined. Each question in the study data may be associated with an identifier. For each group that is being combined, an identifier of the combined question may be generated. The identifier of each question in the group may be replaced with the identifier of the combined question.

At step 440 any missing data may be imputed. The study results retrieved at step 405 may be missing some data. For example, some attribute values might not have been collected for a patient. If too much data is missing from a study, the results of that study may be removed from further use. Each set of study data may be compared to a threshold amount of missing data. The threshold may be selected by testing multiple different thresholds, such as 50%, 55%, and 60%. If the amount of data missing from a set of study data is above the threshold, that study data might not be included in the final dataset. In some instances, rather than removing an entire study, individual attributes or patients within the study may be removed if those attributes have a lot of missing data. For example if a patient, study, or attribute is missing more than 50% of the values, that patient, study, or attribute may be removed from the study data. The missing data may be imputed using various methods, such as multiple imputation by chained equations (MICE).

At step 445 the final dataset 215 may be generated. The transformed results 211-14 from each of the study results 201-04 may be combined to form a single final dataset 215. The questions in the final dataset 215 may all have been standardized, and some of the questions in the final dataset 215 may have been combined. Each datapoint in the final dataset 215 may contain various attributes. The attributes may include responses to questions, any other data regarding the patient, data regarding the treatment that the patient was given, and data regarding the efficacy of the treatment on the patient. The data regarding the efficacy of the treatment on the patient may be referred to as the "label" for the datapoint. The MLA 225 may be trained to predict the label for a datapoint.

At step 450 the final dataset 215 may be split into a training set 220, validation set 221, and/or testing set 222. Each datapoint in the final dataset 215 may be assigned to either the training set 220, validation set 221, and/or testing set 222. Any technique may be used for separating the final dataset 215 into the training set 220, validation set 221, and/or testing set 222, such as randomly selecting datapoints in the final dataset 215 for each of the sets. The training set 220, validation set 221, and/or testing set 222 may be assigned a predetermined amount or proportion of datapoints. For example the training set 220 may include 80% of the datapoints in the final dataset 215, the testing set 222 may include 10% of the datapoints in the final dataset 215, and the validation set 221 may include 10% of the datapoints in the final dataset 215.

At step 455 the training set 220 may be used to select features for the MLA 225. A subset of the attributes in the final dataset 215 may be selected to be used as features by the MLA 225. Features that are likely to be most useful in predicting the efficacy of treatments may be selected. A feature selection process may be applied to the training set 220 to determine which features will be used. Any feature selection algorithm may be used. The feature selection algorithm may output one or more attributes of the final dataset 215 to be used as features.

The features may be selected based on the determined influence of the features on the results of the final predictive objective. For example, in order to predict treatment efficacy, the MLA 225 may be trained to determine the likelihood that a certain prescribed treatment will lead to remission for any given patient. Features may be selected that appear to influence whether the prescribed treatment will lead to remission.

Features may be selected based on intrinsic patterns that exist in the training set 220. The ability of the MLA 225 to associate a treatment efficacy to a patient may be affected by which features are selected. If the selected features are not sufficiently information rich, the performance of the MLA 225 may deteriorate. Features may be selected that align patterns found in the training set 220 with their ability to determine if a treatment will lead a patient to remission. Features having the highest amount of influence may be selected at step 455.

Examples of features that may be contained in the datasets and/or selected are included in Table 1 below. It should be understood that the features listed in Table 1 are exemplary, and that other features may be contained in the datasets and/or generated using the datasets.

This table presents a list of features in a tabulated format.

TABLE 1

| Examples of features | | | |
|---|---|---|---|
| Abuse | Eating disorder | Mobility | Race |
| Addiction symptoms | ECG | Mood | Reactivity |
| ADHD | ECT | Mother treated | Recent life |

16

TABLE 1-continued

| Examples of features | | | |
|---|---|---|---|
| | | violently | stress |
| ADHD symptoms | Educational attainment | Motivation | Reckless overconfidence |
| Adherence | Emotional | Muscular | Recurrent episodes |
| Adjustment disorders | Employment status | Narcissistic | Related to guilt |
| Adopted | Enclosure | Negative symptoms | Relationships |
| Adverse effects | Energy | Neglect | Residence |
| Age | Engagement/interest | Neuro-developmental and related disorders | Respiratory |
| Age first received psychiatric treatment | Ethnicity | Neurological | Respiratory rate |
| Age of MDD onset | Euphoric activation | Neuromodulation | Restrictive eating |
| Age of onset | Excoriation disorder | Neuroticism | Romantic |
| Agoraphobia | Executive Function | Non-biological family | rTMS |
| Agoraphobic | Exercise | Number of acts | Rumination |
| Alcohol | Family | Number of children | Rural/urban |
| Anger | Family history | Number of cigarettes per day | Sadness |
| Anhedonia | Fear | Number of cigars per day | Satisfaction with medication |
| Anorexia nervosa | Frequency | Number of cups per day | Schizoaffective disorder |
| Antisocial | Functional impairment | Number of drinks per week | Schizoid |
| Anxiety | Future | Number of episodes | Schizophrenia |
| Anxiety symptoms | Gambling | Number of hospitalizations | Schizotypal |
| Appetite | Gastrointestinal | Number of pipes per day | School/work |
| Auditory | Gender | Number of previous attempts | Seasonal-related |
| Autism spectrum | Gender dysphoria | Number of previous episodes | Self care |
| Autonomic | Generalized anxiety disorder | Numbing | Self-appraisal |
| Avoidance | Genes | Obsession | Self-harm |
| Avoidant | Genito-urinary | Obsessive compulsive | Self-referential thinking |
| Avoidant restrictive food intake disorder | Grandiose | Obsessive compulsive and related disorder | Self-worth |
| Being punished | Guilt | Obsessive compulsive and related disorders | Sensation of heaviness in limbs or back or head |
| Binge eating disorder | Hallucination | Obsessive compulsive symptoms | Sensitivity |
| Binging | Hallucinations | OCD | Sensory |
| Biofluids | Handedness | Olfactory/Tactile/Gustatory | Severity |
| Biological family | Head circumference | Oppositional defiant disorder | Severity/tolerability |
| Bipolar disorder | Headache | Optimism/Pessimism | Sex |

TABLE 1-continued

| Examples of features | | | |
| --- | --- | --- | --- |
| Blood pressure | Health-related | Orphanage/foster care experience | Sexual |
| BMI | Heart rate | OSFED | Sleep |
| Body dysmorphia | Heart rate variability | Other | Smoking status |
| Body fat percentage | Height | Other caffeinated beverages | Social |
| Body Temperature | Hip circumference | Other major affective disturbance | Sociodemographic |
| Borderline | Histrionic | Other psychotic disturbance | Socioeconomic status |
| Boredom | Hopelessness | other specified ADHD | Somatic |
| Bulimia nervosa | Hormone replacement therapy | Other specified obsessive compulsive and related disorder | Specific phobia |
| Bullying | Hospitalization | Other specified tic disorder | Standard |
| Caffeine consumption | Hospitalization specifically for suicide | Outlook | States and Traits |
| Cardiac | Hospitalized for any psychiatric disturbance | Outpatient | Stress disorders |
| Children | Hostility | Overwhelm | Stress/trauma |
| Chromosomal abnormality | Household activities | Pain | Substance abuse |
| Classes | Household dysfunction | Panic attacks | Substance abuse-alcohol |
| Clinician-patient relationship | Hyperactive cognition | Panic disorder | Substance abuse-drugs |
| Cluster A | Hyperarousal | Paranoia | Substance use |
| Cluster B | Hypersomnia | Paranoid | Substance use disorder |
| Cluster C | Hypomania | Parents | Substance-related |
| Coffee drinking | Immigrant status | Partial hospitalization | Suicidal ideation |
| Cognitive | Impulsivity | Paternal | Suicidality |
| Cognitive symptoms | Incarcerated relative | Persistent/chronic tic disorder | Suicide |
| Combined presentation | Incarceration | Personal | Suicide attempts |
| Concentration | Increased appetite | Personal history | Symmetry/ordering/arranging |
| Condition | Inpatient | Personality disorder | Systolic |
| Confusion | Insight | Pervasive developmental disorder | tDCS |
| Contamination/cleaning | Insomnia | Pharmacology | Tension |
| Contraception | Intellectual disability | Phobia | Thoughts and beliefs |
| Country of origin | Intensity | Physical | Tic disorder |
| Crying | Interpersonal | Physical activity | Tic symptoms |
| CYP1A2 | Interval between remission of last episode to start of current episode | Physiology | Time since first episode of MDD |
| CYP2B6 | Intrusions | Planning | Tourette's syndrome |
| CYP2C19 | IQ | Positive symptoms | Traumatic brain injury |
| CYP2D6 | Irritability | Post traumatic stress | Treatment |

TABLE 1-continued

| Examples of features | | | |
| --- | --- | --- | --- |
| CYP3A4POR | Laboratory values | Post-childhood trauma | Trembling/shaking |
| Decision making | Lassitude | predominantly hyperactive/impulsive presentation | Trichotillomania |
| Decreased appetite | Late | predominantly inattentive presentation | Trichotillomania symptoms |
| Delusion | Legal | Pregnancy | Trouble relaxing |
| Delusional disorder | Leisure | Pregnancy-related | Type 1 |
| Delusions | Level of social support | Premenstrual dysphoric disorder | Type 2 |
| Dependent | Life satisfaction | Preparatory acts | Type of care |
| Depression | Living arrangement | Previous episodes | Type/arrangement |
| Depression secondary to another cause | Loneliness | Primary language spoken | Unspecified ADHD |
| Diastolic | Major depressive disorder | Provisional tic disorder | Unspecified eating disorder |
| Disordered eating symptoms | Mania | Psychiatric | Unspecified obsessive compulsive and related disorder |
| Disorganization | Manic episodes | Psychiatric medication | Unspecified tic disorder |
| Dissociation | Marital status | Psychic | Variation |
| Diurnal | Maternal | Psychomotor agitation | Violence |
| Divorce | Medical | Psychomotor arousal | Violent/sexual/religious content |
| Dizziness/Lightheadedness | Medication response | Psychomotor retardation | Visual |
| Doubting/checking | Memory | Psychotherapy | Vomiting |
| Drugs | Menopausal status | Psychotic disorders | Waist circumference |
| Due to another medical condition | Menstrual-related | Psychotic symptoms | Waist/hip ratio |
| Duration | Menstruation | PTSD | Weight |
| Duration of last episode | Mental deficiency | Public | Weight gain |
| Duration of living at current residence | Mental illness | Purging | Weight loss |
| Dysthymia | Metabolizer status i.e. normal or poor or rapid | Quality of life | Working memory |
| Early | Method | Quality of mood | Worry |
| Early life stress | Middle | Quitting status | Years of smoking Years since immigration |

At step 460 the MLA 225 may be trained using the training set 220 and the features selected at step 455. The MLA 225 may be trained with the objective of accurately predicting remission rates for each treatment in the final dataset 215. The MLA 225 may receive the training set 220 of datapoints. For each datapoint in the training set 220, the MLA 225 may predict, based on the features, a likelihood that each treatment will lead the patient to remission. The predicted likelihood for the treatment that was actually given to the patient during the study may be compared to the label for the datapoint. The label indicates whether or not, during the study, the treatment led to remission. A loss function may be used to compare the label to the prediction output by the MLA 225. The MLA 225 may be adjusted based on a difference between the predicted likelihood and the label. In this manner, the MLA 225 may be trained to receive a datapoint including the features selected at step 455 and output a predicted likelihood that each treatment will lead the patient to remission.

The loss function may be composed of various subsections that act as regularizers and controls for the intended behaviour of the MLA 225. The global loss which may be used to train the overall MLA 225 may be a weighted summation of some or all of the following components:

(1) The remission classification on whether or not the likelihood of remission for a given treatment matches the true occurrence (target) for that patient. This may be characterized as a cross-entropy loss function.

(2) The autoencoder loss may be defined by the Euclidean distance between the original sample, x, and the decoded sample, d(e(x)). Other distance metrics may be used, such as, but not limited to, changes in the entropy between the distributions and Wasserstein distance.

(3) Controlling for the prototype-sample distance variance. The variance of the distance between prototypes and samples can be composed up of both (I) the (intra) variance of the distances between the nearest samples for a given prototype and the prototype itself and/or (II) the (inter) variance of the pairwise distances between all of the prototypes. These two components may be linearly combined with coefficients that can modulate their impact on the global objective. This may control the prototypes with the objective being that the prototypes are sufficiently spread out across the latent sample space so as to potentially capture topically useful and mutually independent properties of the original patient population. For scenarios where the prototypes are learned during the training process, this component may cause the prototypes to be spread out so as to not produce redundant prototypes which might not resemble and/or correctly capture the nuances and characteristics of real patients.

(4) Controlling for differential treatment remission prediction for a prototype. The differential prototype remission variance loss can be composed of both (I) the (inter) variance in remission predictions between different prototypes across all treatment types and (II) the (intra) variance within prototypes and between predictions of different treatments. These may be linearly combined through a weighted summation that allows for a customizable configuration between these loss components. Since the objective function may encourage greater variance across these two domains, this component of the loss function may be negated to induce that behavior during the training cycles.

A weighting coefficient may be assigned to each of the loss components defined above. For example the weighting coefficients may be as follows: (1) 1, (2) 0.01, (3.I) 0.001, (3.II) 0.01, (4) 0.01 [whose internal module coefficient composition may be (4.I) 0.05, (4.II) 0.95]. The performance of the classification problem, which is loss component (1) above, may be prioritized above all other loss components such as by assigning the largest weight to that component. The classification problem may be assigned the largest weight as this loss component corresponds to predicting the remission rates for each of the assigned drugs. By increasing the weight of this component, the accuracy of remission predictions by the MLA 225 may be improved.

The weightings for the components (2) to (4) may affect how the patient samples are spread across the prototypes using the variance. The weightings for these components may be configured using trainable parameters. The values of these weightings may be continuously updated during the MLA 225 raining process in order to optimize the downstream objectives (e.g. supervised/unsupervised/reinforcement objectives as applied to mental health outcomes).

The Adam optimizer may be used to dictate the training of the MLA 225 and/or any other suitable optimizer may be used to train the MLA 225. The optimizer may use the training set 220 and the features selected at step 455 to train the MLA 225. The optimizer may configure all trainable parameters of the MLA 225, such as the auto-encoder, the prototypes, and/or the predictive downstream layer(s). The optimizer may pass the datapoints from the training set 220 through the MLA 225, calculate the individual loss components for each datapoint, determine changes to be made to the parameters to minimize each of the loss components, and repeat this process to minimize the global loss.

The previously described loss components form a series of sub-optimization problems used by the global optimizer to determine if the existing parameters are optimally set so as to perform well at each of those sub-problems. The optimizer keeps track of each operation that takes place between each data and parameter so that for each training cycle, it can determine the proportional amount of changes to make to each independent parameter to minimize the downstream loss components. The proportion of changes that is done for each cycle of learning (otherwise known as the learning rate), is a hyperparameter that is set for the optimizer which affects the speed at which it can explore the plausible solution space to output an optimal MLA 225. The learning rate may be predetermined. For example, the learning rate may be set to 0.0001. This may optimize the results to ensure the MLA 225 can learn differential treatment benefit.

The trained MLA 225 may be adjusted using the validation set 221 at step 465. The trained MLA 225 may be tested using the testing set 222 at step 470. An amount of loss may be calculated for each of the datapoints in the testing set 222. The amount of loss may indicate a difference between the label of a datapoint and the prediction output by the MLA 225 for that datapoint. An average amount of loss may be determined for all of the datapoints in the testing set 222. If the average amount of less is below a pre-determined threshold, the MLA 225 may be considered to be ready for use.

After the MLA 225 is trained, the MLA 225 may be used to predict treatment efficacy for a patient. Questionnaire responses corresponding to the patient may be received. The questionnaire responses may have been completed by the patient and/or a clinician. The questionnaire completed by the patient may be a standardized clinical questionnaire. The questionnaire may have been generated based on the features used to train the MLA 225.

The questionnaire responses may be input to the MLA 225. Other data corresponding to the patient may also be input to the MLA 225, such as physiological data, historical data, sociodemographic data, psychological data, and/or any other relevant data regarding the patient. The MLA 225 may output a predicted efficacy of each treatment that the MLA 225 was trained to predict. An interface may be generated using the predicted efficacies. The interface may display all of the available treatment options and the predicted efficacy, for the patient, of each of the treatment options. The interface may be output to be displayed on a screen and/or monitor.

The invention claimed is:

1. A method comprising:
retrieving a plurality of study results, wherein each study result comprises a plurality of datapoints, wherein each datapoint corresponds to an individual, and wherein each datapoint comprises a plurality of attributes of the individual and outcome data corresponding to a treatment received by the individual;
extracting a plurality of questions from the plurality of study results, wherein the plurality of questions comprises questions from questionnaires given to individuals enrolled in each study of the plurality of studies;
converting each question of the plurality of questions into questions in a standardized format;
assigning one or more categories to each of the plurality of questions;
determining, based on the one or more categories assigned to each question, a plurality of groups of questions;
determining a response scale to use for each group of the plurality of groups;
rescaling responses to the groups of questions based on the respective response scale of the group;
combining questions for each group of the plurality of groups;
imputing missing attribute values in the plurality of study results;
generating a final dataset by combining the plurality of study results;
assigning a label to each datapoint of the final dataset, wherein the label indicates the outcome data of the individual corresponding to the respective datapoint;
splitting the final dataset into a training set, validation set, and testing set;
selecting, based on the training set, a plurality of features in the training set; and
training a machine learning algorithm (MLA) comprising a neural network using the plurality of features of the training set, wherein the training comprises:
  encoding, by an encoder, values of the plurality of features to form vectors for each datapoint of the training set,
  inputting the vectors to the MLA,
  outputting, by the MLA, a predicted efficacy of a treatment for each datapoint of the training set,
  determining an amount of loss for each datapoint of the training set using a loss function that compares the predicted efficacy of the treatment for each datapoint of the training set to the label for the respective datapoint, and
  adjusting the neural network to reduce the amount of loss between the predicted efficacy of the treatment for each datapoint of the training set and the label for the respective datapoint, thereby optimizing the predicted efficacy of the treatment output by the MLA;
receiving questionnaire responses corresponding to an individual;
inputting the questionnaire responses into the MLA;
outputting, by the MLA, a predicted efficacy of the treatment for the individual;
generating, based on the predicted efficacy of the treatment, an interface; and
outputting for display the interface.

2. The method of claim 1, wherein the questionnaires comprise clinical questionnaires given to patients enrolled in clinical trials.

3. The method of claim 1, wherein each datapoint corresponds to a patient enrolled in a clinical trial, and wherein the plurality of attributes comprise an indication of a treatment given to the patient.

4. The method of claim 3, wherein the plurality of attributes comprise an indication of responses to a clinical questionnaire given to the patient.

5. The method of claim 3, wherein the plurality of attributes comprise an indication of whether the treatment is effective for the patient.

6. The method of claim 3, wherein the plurality of attributes comprise an indication of side effects experienced by the patient.

7. The method of claim 3, wherein the plurality of attributes comprise physiological data of the patient.

8. The method of claim 3, wherein the plurality of attributes comprise historical data of the patient.

9. The method of claim 3, wherein the plurality of attributes comprise sociodemographic data of the patient.

10. The method of claim 3, wherein the plurality of attributes comprise psychological data of the patient.

11. The method of claim 3, wherein rescaling responses to the groups of questions comprises using equipercentile scaling to rescale the responses.

12. A method comprising:
retrieving a plurality of study results, wherein each study result comprises a plurality of datapoints, wherein each datapoint corresponds to an individual, and wherein each datapoint comprises a plurality of attributes of the individual and outcome data corresponding to a treatment received by the individual;
extracting a plurality of questions from the plurality of study results, wherein the plurality of questions comprises questions from questionnaires given to individuals enrolled in each study of the plurality of studies;
converting each question of the plurality of questions into questions in a standardized format;
assigning one or more categories to each of the plurality of questions;
determining a group of questions, of the plurality of questions, that have a same set of assigned categories;
combining the group of questions;
generating a final dataset by combining the plurality of study results;
assigning a label to each datapoint of the final dataset, wherein the label indicates the outcome data of the individual corresponding to the respective datapoint;
selecting a plurality of features in the final dataset; and
training a machine learning algorithm (MLA) comprising a neural network using the plurality of features, wherein the training comprises:
  encoding, by an encoder, values of the plurality of features to form vectors for each datapoint of the training set,
  inputting the vectors to the MLA,
  outputting, by the MLA, a predicted efficacy of a treatment for each datapoint of the training set,
  determining an amount of loss for each datapoint of the training set using a loss function that compares the predicted efficacy of the treatment for each datapoint of the training set to the label for the respective datapoint, and
  adjusting the neural network to reduce the amount of loss between the predicted efficacy of the treatment for each datapoint of the training set and the label for the respective datapoint, thereby optimizing the predicted efficacy of the treatment output by the MLA;

receiving questionnaire responses corresponding to an individual;

inputting the questionnaire responses into the MLA;

outputting, by the MLA, a predicted efficacy of the treatment for the individual;

generating, based on the predicted efficacy of the treatment, an interface; and outputting for display the interface.

13. The method of claim 12, wherein combining the group of questions comprises:

determining a response scale for the group of questions; and rescaling responses corresponding to the group of questions based on the response scale.

14. The method of claim 12, wherein the questionnaires comprise clinical questionnaires given to patients enrolled in clinical trials.

15. The method of claim 12, wherein each datapoint corresponds to a patient enrolled in a clinical trial, and wherein the plurality of attributes comprise an indication of a treatment given to the patient.

16. The method of claim 15, wherein the plurality of attributes comprise an indication of whether the treatment is effective for the patient.

17. The method of claim 15, wherein the plurality of attributes comprise an indication of side effects experienced by the patient.

18. A method for predicting treatment efficacy for a patient, the method comprising:

training a machine learning algorithm (MLA) comprising a neural network by:

retrieving a plurality of study results corresponding to a plurality of treatments, wherein each study result comprises a plurality of datapoints, wherein each datapoint corresponds to an individual, and wherein each datapoint comprises a plurality of attributes of the individual and outcome data corresponding to a treatment received by the individual, extracting a plurality of questions from the plurality of study results, wherein the plurality of questions comprise questions from questionnaires given to individuals enrolled in each study of the plurality of studies, converting each question of the plurality of questions into questions in a standardized format, assigning one or more categories to each of the plurality of questions, determining a group of questions, of the plurality of questions, that have a same set of assigned categories, combining the group of questions, generating a final dataset by combining the plurality of study results, assigning a label to each datapoint of the final dataset, wherein the label indicates the outcome data of the individual corresponding to the respective datapoint; and training the MLA using the final dataset, wherein the training comprises:

encoding, by an encoder, values of each datapoint of the training set to form vectors, inputting the vectors to the MLA, outputting, by the MLA, a predicted efficacy of a treatment for each datapoint of the training set, determining an amount of loss for each datapoint of the training set using a loss function that compares the predicted efficacy of the treatment for each datapoint of the training set to the label for the respective datapoint, and adjusting the neural network to reduce the amount of loss between the predicted efficacy of the treatment for each datapoint of the training set and the label for the respective datapoint, thereby optimizing the predicted efficacy of the treatment output by the MLA;

receiving questionnaire responses from the patient;

inputting the questionnaire responses into the MLA;

outputting, by the MLA, a predicted efficacy of each of the plurality of treatments;

generating, based on the predicted efficacy of each of the plurality of treatments, an interface; and outputting for display the interface.

19. The method of claim 18, wherein the plurality of attributes comprise an indication of side effects experienced by the patient.

20. The method of claim 18, wherein the interface displays one or more treatment options and a prediction corresponding to each of the one or more treatment options.

* * * * *